United States Patent [19]

Pagani

[11] 4,208,347
[45] Jun. 17, 1980

[54] PROCESS FOR THE SYNTHESIS OF UREA

[75] Inventor: Giorgio Pagani, Milan, Italy

[73] Assignee: Montedison S.p.A., Milan, Italy

[21] Appl. No.: 901,816

[22] Filed: May 1, 1978

[30] Foreign Application Priority Data

| May 5, 1977 | [IT] | Italy | 23213 A/77 |
| May 5, 1977 | [IT] | Italy | 23214 A/77 |
| May 18, 1977 | [IT] | Italy | 23710 A/77 |
| May 18, 1977 | [IT] | Italy | 23711 A/77 |

[51] Int. Cl.$^2$ .......................................... C07C 126/02
[52] U.S. Cl. .............................................. 260/555 A
[58] Field of Search ................................ 260/555 A

[56] References Cited

U.S. PATENT DOCUMENTS

| 3,049,563 | 8/1962 | Bochinski | 260/555 A |
| 3,356,723 | 12/1967 | Kasenbrood | 260/555 A |
| 3,867,442 | 2/1975 | Logemann | 260/555 A |
| 3,984,469 | 10/1976 | Guadalupi | 260/555 A |
| 4,001,320 | 1/1977 | Kaasenbrood | 260/555 A |
| 4,012,443 | 3/1977 | Bonetti | 260/555 A |
| 4,013,718 | 3/1977 | Guadalupi | 260/555 A |
| 4,036,878 | 7/1977 | Kaasenbrood et al. | 260/555 A |

FOREIGN PATENT DOCUMENTS

| 1468628 | 2/1969 | Fed. Rep. of Germany | 260/555 A |
| 1184004 | 3/1970 | United Kingdom | 260/555 A |

*Primary Examiner*—Brian E. Hearn
*Attorney, Agent, or Firm*—Stevens, Davis, Miller & Mosher

[57] ABSTRACT

An improved isobaric double-recycle process is disclosed for synthesizing urea with the formation of ammonium carbamate as an intermediate, comprising effecting reaction between ammonia and carbon dioxide at high $NH_3:CO_2$ molar ratios, a heat-treatment of the synthesis product at substantially the same pressure as that of the synthesis step and in the presence of a stripping gas, and two distinct isobaric recycles of the residual substances and of the substances in excess released from said synthesis product, said process being characterized in that:

(a) said heat-treatment of the synthesis product is carried out in two consecutive stages which are isobaric or substantially isobaric with respect to the synthesis step, in the first of which stages said synthesis product is heated, whereby substantially all the residual ammonium carbamate is decomposed and the decomposition products are displaced together with part of the excess $NH_3$, while in the second stage the remaining part of the $NH_3$ excess is displaced by supplying supplemental heat and by injecting thereto a $CO_2$ stream; and (b) the gas phase stripped in the first stage is immediately recycled to the synthesis step and the gas phase stripped in the second stage is subjected to a condensation and to a residual gas purge and then recycled, in the liquid state, to the synthesis step.

The synthesis temperature may range from 170° to 205° C., the synthesis pressure from between 100 and 250 Kg/cm$^2$, and the $NH_3:CO_2$ molar ratio during the synthesis from 2.5:1 to 10:1.

Suitable apparatus for carrying out the process is also disclosed.

15 Claims, 4 Drawing Figures

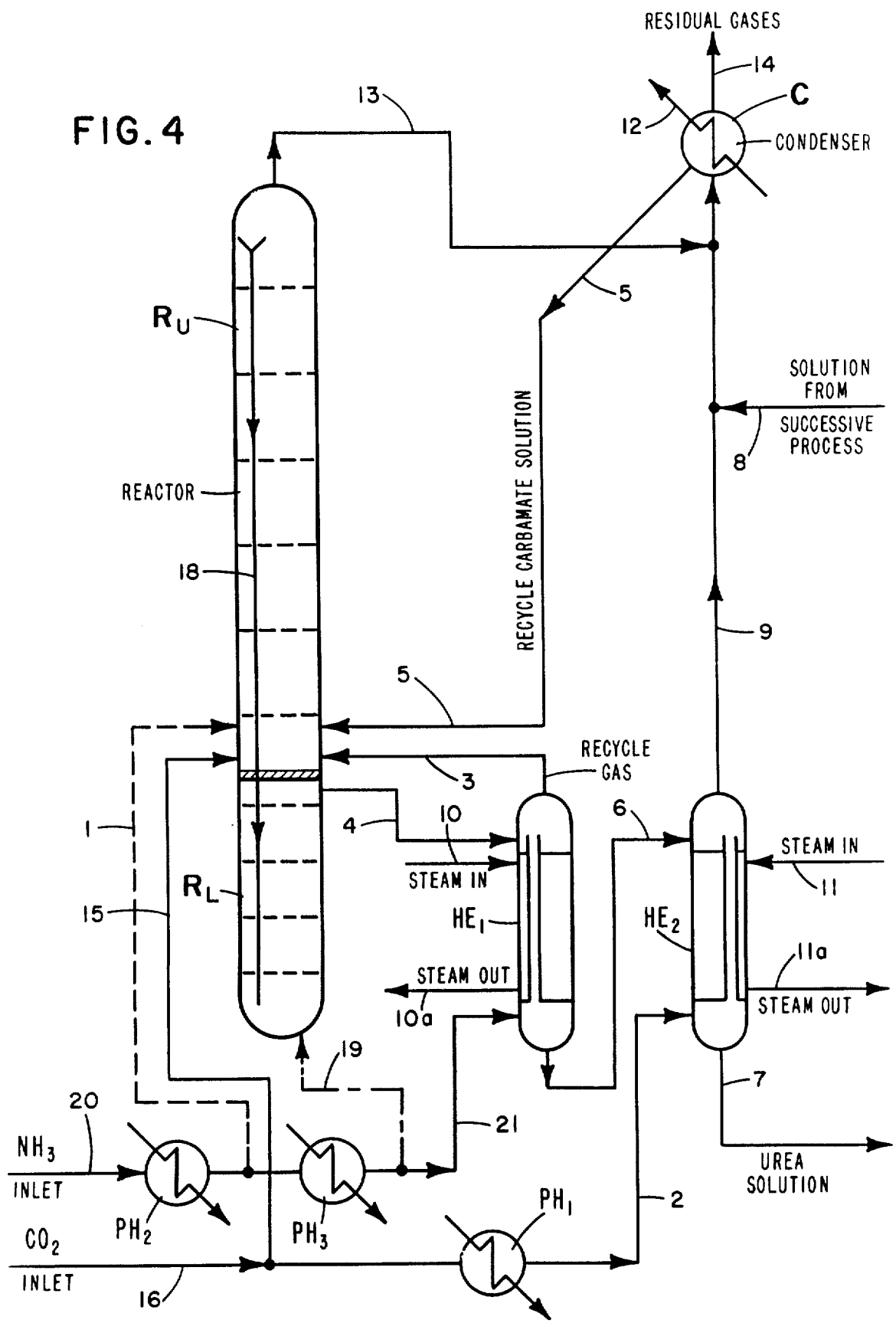

PROCESS FOR THE SYNTHESIS OF UREA

This invention relates to an improved process for the synthesis of urea from ammonia and carbon dioxide, with an isobaric double recycle, and with the intermediate formation of ammonium carbamate, according to the equation:

$$2NH_3 + CO_2 \rightleftharpoons NH_2COONH_4 \rightleftharpoons NH_2CONH_2 + H_2O$$

The first of these reactions is exothermic, while the second is slightly endothermic.

It is well known that the conversion of ammonium carbamate to urea is not quantitative and that the residual ammonium carbamate is usually decomposed into the starting compounds, $NH_3$ and $CO_2$, which are recycled to the synthesis according to different methods which characterize this general type of process.

According to U.S. Pat. No. 3,356,723, a small excess of $NH_3$ is used with a molar ratio $NH_3:CO_2$ in the reactors of between 2.5:1 and 3:1. The decomposition of the ammonium carbamate and the displacement of the excess $NH_3$ from the liquid product to the gaseous phase are carried out by subjecting the product, at the synthesis pressure and in a thin-layer heat exchanger (falling film stripper, according to the English terminology), to heat and a stream of $CO_2$ as stripping agent. This patent also contemplates the immediate recycle to the synthesis of said gaseous phase; the equal pressure employed in the synthesis and the stripping zones has suggested defining this process as an "isobaric total recycle process". Although it represents a certain step forward in comparison with the prior art prior to that time, nevertheless this process has some drawbacks. The quantity of stripping gas is in fact limited to the stoichiometric $CO_2$ requirement and the amount of substance that can be displaced from the liquid phase to the gaseous phase is therefore limited unless vigorous heating is employed, which however involves excessive consumption of high pressure steam. The $NH_3$ excess in the synthesis zone must therefore be kept below a certain level and cannot exert all the known beneficial influence on the course of the synthesis. The yields are not very high (55–60%) and consequently the quantities of residual ammonium carbamate in the solution leaving the reactor reach rather high levels.

Besides the foregoing, there are other processes based on $NH_3$ stripping (see for instance U.S. Pat. No. 3,049,563 and Italian Pat. No. 684,929). These processes can work at higher $NH_3:CO_2$ molar ratios (3.5–3.8) and thus will allow one to obtain greater conversion yields (62–64%) of the desired product. The advantage of a greater yield, however, is annulled by the greater amount of $NH_3$ present in the urea solution leaving the stripper (22–25% $NH_3$ and 5–6% $CO_2$ by weight), which therefore requires too large an $NH_3$ recovery section operating at low pressures, usually 18–20 atmospheres. Consequently, these stripping processes, although offering appreciable advantages, due to the decomposition of a great part of the residual ammonium carbamate at synthesis pressure, are not free from shortcomings owing to the choice of the stripping agent and to the relatively low conversion yield in the reactor.

An object of this invention is to reduce the extent of the drawbacks mentioned above. Still other objects will become even more evident from the following detailed description of the invention.

In its broadest form the present invention resides primarily in an isobaric double-recycle process for synthesizing urea, via the intermediate formation of ammonium carbamate, comprising the reaction between ammonia and carbon dioxide at high $NH_3:CO_2$ molar ratios, a heat-treatment of the synthesis product, substantially at the same pressure as the synthesis pressure and in the presence of a stripping gas, and two distinct isobaric recycles of the residual substances and of the substances in excess released from said synthesis product; said process being characterized in that:

(a) said heat-treatment of the synthesis product is carried out in two consecutive stages which are isobaric in respect of the synthesis, in the first of which stages said synthesis product is heated, whereby substantially all of the residual ammonium carbamate is decomposed and the decomposition products are displaced together with part of the excess $NH_3$, while in the second stage the remaining part of the excess $NH_3$ is displaced by supplying supplemental heat and by injecting thereto a $CO_2$ stream; and (b) the gas phase stripped in the first stage is immediately recycled to the synthesis and the gas phase stripped in the second stage is subjected to a condensation and to a residual gas purge before being also recycled, in the liquid state, to the synthesis.

The synthesis temperature ranges from 170° to 205° C., and preferably from 180° to 200° C. The higher the temperature, the easier becomes the successive stripping of the gases by means of the $CO_2$ stream and the lesser the heat required for the stripping.

The synthesis pressure is between 100 and 250 kg/cm², and preferably between 180 and 225 kg/cm², the higher pressures being preferred in the case of the higher temperatures.

According to one particular embodiment, the ammonia feed is preheated and the $CO_2$ stream fed to the second treatment stage constitutes between 10 and 100% of the synthesis requirement. Preferably the range is from 50 to 90%, the remaining part being fed directly to the synthesis or to the first stripping zone.

The process according to the present invention may be modified by additional new and improving changes without departing from the spirit of the invention. For instance, the synthesis of the urea may be carried out in two different subsequent and superimposed reaction zones, to the first of which, overlying the second, the two isobaric recycles are fed, whereby the dehydration to urea of the greater part of the ammonium carbamate is performed, while in the second zone, operating at $NH_3:CO_2$ molar ratios equal to or higher than those of the preceding zone, the completion of the dehydration is carried out, substantially until the equilibrium level is reached. Further, the decomposition of the ammonium carbamate in the first stage of the isobaric treatment may be improved, under certain operating conditions, by the injection of a certain amount of stripping ammonia.

The $NH_3:CO_2$ molar ratio during the synthesis ranges from 2.5 to 10, and preferably from 4 to 7.

When the synthesis is performed in two different (superimposed) zones, the aforesaid molar ratio is preferably from 4 to 7 in the first and upper most zone and from 5 to 8 in the second. In such event, the residence time of the synthesis mixture in the second and lower-most zone is from 3 to 15, and preferably from 5 to 8 minutes.

The process according to this invention allows one to obtain an urea solution almost free from residual $NH_3$ and $CO_2$, and this has been possible heretofore only at the cost of excessive heat consumption, when the $NH_3:CO_2$ ratio in the reaction zone is too low owing to low yields and to high amounts of ammonium carbamate to be decomposed. Even if the heat was partially recovered in a condenser, the heat recovery occurred at a lower temperature and thus involved a rise in entropy. When on the other hand, high $NH_3:CO_2$ molar ratios were employed, the yields were better, but the amount of residual $NH_3$ in the urea solution was excessive, which led to an undesired increase in both the number and the volume of the apparatus elements located downstream of the isobaric cycle.

It is the great merit of the present invention that it reconciles two heretofore contrasting requirements: on the one side the need to obtain solutions practically free from residual reagents and on the other side the need to employ high $NH_3:CO_2$ molar ratios in order to obtain higher yields and lower heat consumption.

Another advantage of this invention resides in the extreme ease of controlling the not-infrequent thermal disturbances, of a temporary and oscillating nature, described in Dutch Patent Publication No. 68/8472. Thus, by suitably proportioning the streams coming from the first and second stripping stages, it is possible to readily achieve an optimum thermal profile throughout the system whereby to stabilize the temporary phenomena just mentioned.

When the synthesis is carried out in two different (superimposed) zones, pre-heated ammonia fed to the lower zone of the synthesis increases the $NH_3:CO_2$ molar ratio in said lower reaction zone to a value above the level of said ratio in the preceding upper zone. By thus increasing the $NH_3:CO_2$ molar ratio, the level of the ammonium carbamate dehydration is raised because of the dehydrating effect of ammonia, which combines with the resulting water of reaction and forms a little dissociated ammonium hydroxide ($NH_4OH$) thus promoting the completion of the synthesis.

In general, an increase in the $NH_3:CO_2$ molar ratio involves some negative aspects, such as for instance the resulting necessity to operate at higher pressures and at reduced temperatures (a necessity associated with the greater $NH_3$ excess) and the consequently greater consumption of heat required for the displacement and recycling of said greater excess of $NH_3$. If one wishes to overcome these drawbacks, the optimal value of the $NH_3:CO_2$ molar ratio should not, according to current opinion, exceed 5:1.

In accordance with the present invention, however, it has now been discovered that it is possible to further increase, and with advantage, the $NH_3:CO_2$ molar ratio up to 7:1 or even more, provided the increase be in the second and lowermost of the two synthesis zones. The partial pressure of ammonia above the liquid phase in the lower synthesis zone may be greater, with respect to that in the upper zone, by an amount corresponding to about the partial pressure of the inert gases, plus the pressure corresponding to the overlying liquid column. It is this that allows one to increase the $NH_3:CO_2$ molar ratio up to 7:1 or even more and thus the conversion yield of the ammonium carbamate, a yield that can reach very high values for instance 80% and even more. Of course, the greater excess of ammonia solubilized in the liquid phase must be recovered in the first of the two stripping stages and then fed to the uppermost synthesis zone; an intermediate value of the $NH_3:CO_2$ molar ratio, for instance between 5:1 and 8:1, may be obtained by feeding part of the preheated ammonia to the uppermost zone and part to the lowermost one.

The improved process of the present invention is still further illustrated by the accompanying four figures wherein:

FIG. 4 is an alternative modification of FIG. 2, showing the addition of an ammonia injection feature into the first stripping zone of that figure.

Figure 1:
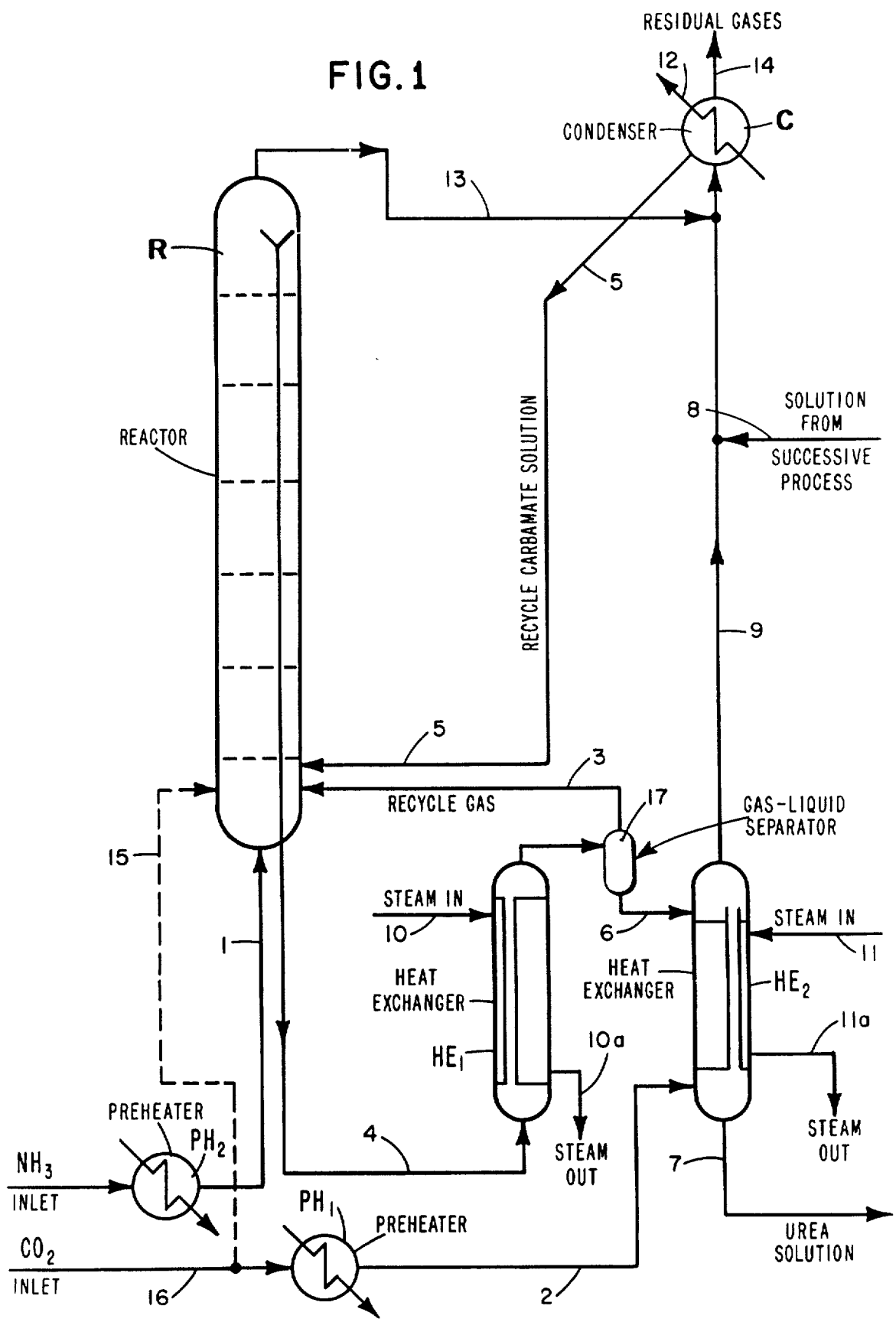
FIG. 1 represents a flowsheet of the process.

According to FIG. 1, urea is synthesized in a vertical cylindrical reactor R equipped with conventional sieve trays in order to maintain the axial flow homogeneous or uniform throughout the reactor thus avoiding any back-mixing of the reaction liquid.

The intermediate liquid product overflows, due to gravity, through pipe 4, and into a conventional vertical tube bundle heat exchanger $HE_1$, with inlet from the bottom, heated by steam via lines 10 and 10a, where the residual ammonium carbamate is almost completely decomposed. The decomposition gases and a portion of the excess $NH_3$ flow back to the reactor R through pipe 3 after separation from the liquid in gas-liquid separator tank 17. The liquid (solution) from the separator 17 passes to a second exchanger $HE_2$ via line 6 which is a conventional falling film stripper, heated with steam via lines 11 and 11a. In this second heat exchanger $HE_2$, 75% of the required $CO_2$ introduced thereto via line 16 and 2, and preheated in the preheater $PH_1$, removes almost all the residual $NH_3$ and the solution flowing out from the bottom of heat exchanger $HE_2$ passes, through pipe 7, to further and usual process steps for purifying the urea product.

The gaseous stream leaving the top of the second stripper $HE_2$ flows via line 9 into a condenser C together with the gases coming from the top of the reactor R via line 13 and with a solution coming from successive process steps via line 8. The heat of condensation brings about the production of steam which leaves the condenser C via line 12.

Residual gases are purged from the condenser C through pipe 14, while the solution which is recycled to the reactor R leaves the condenser C by gravity flow through pipe 5.

The $NH_3$ feed preheated in the preheater $PH_2$ is conveyed to the bottom of the reactor R through pipe 1. Pipe 15, branching off from header 16, conveys the remaining 25% of the required $CO_2$, without preheating, directly to the reactor R.

Figure 3:
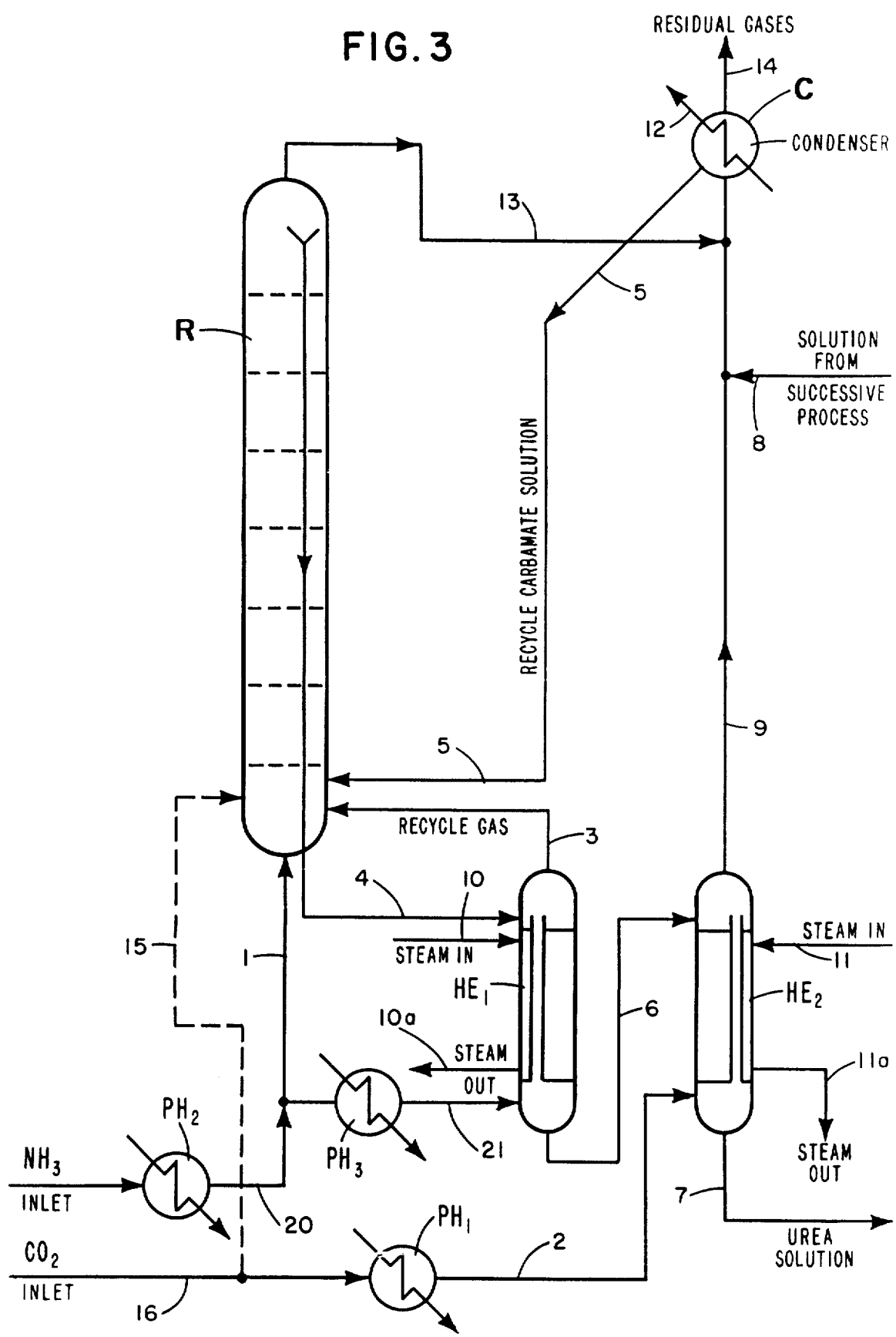
FIG. 3 illustrates the addition of an ammonia injection feature into the first stripping zone.

The first stripper or heat exchanger $HE_1$ may alternatively be of the conventional falling film type, as indicated for instance by FIGS. 3 and 4.

Figure 2:
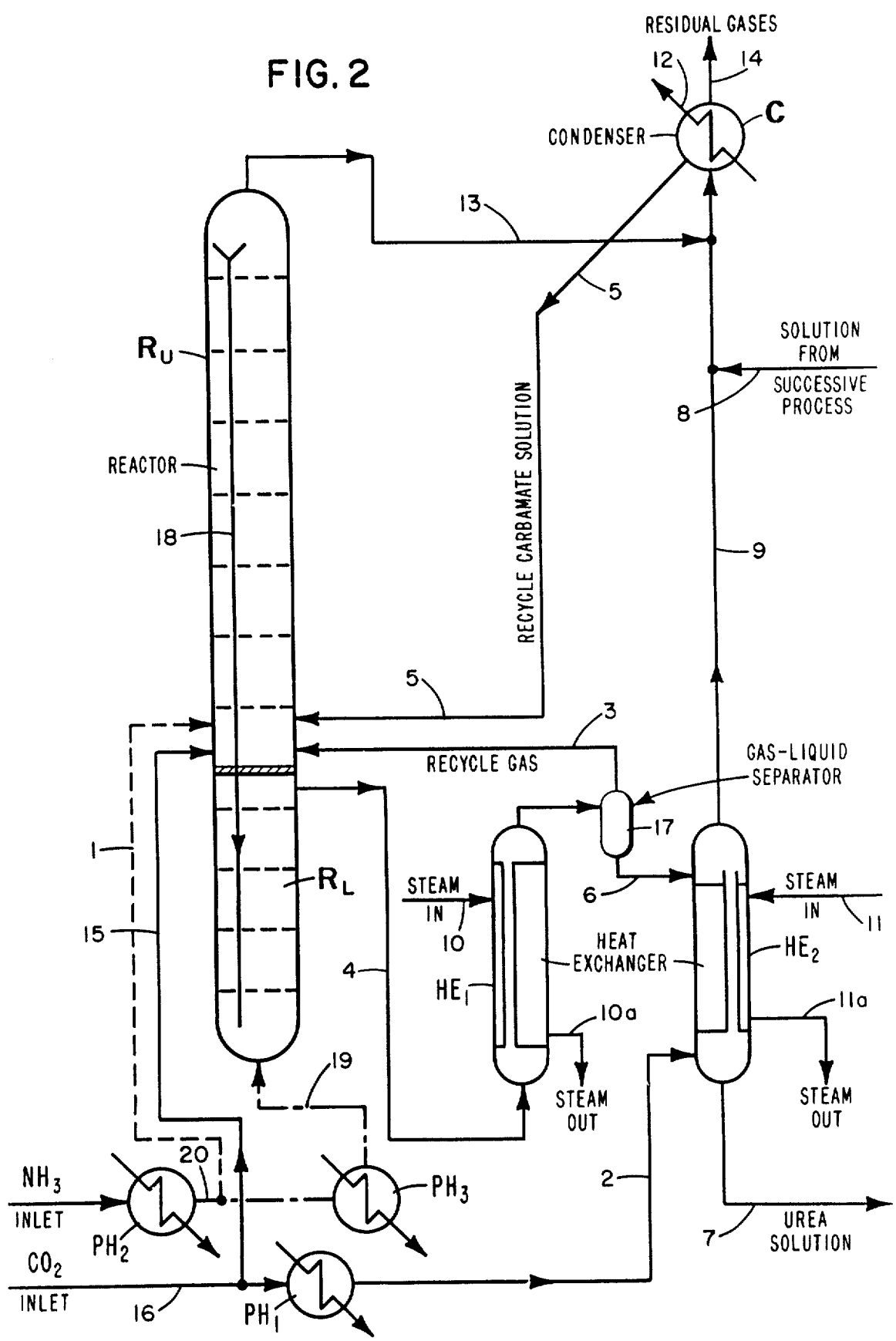
FIG. 2 illustrates a modification consisting of splitting the synthesis zone into two superimposed synthesis zones.

The remaining FIGS. 2, 3 and 4 are self-explanatory but in any event are exhaustively described in Examples 3, 8 and 10 below.

Besides the process, the present invention also relates to a particularly desirable apparatus for carrying out the same. Referring to FIG. 1 again, this apparatus basically comprises:

(a) a cylindrical and vertical reactor R equipped with devices for the introduction through pipe 1, of a feed stream; another optional inlet nozzle connected with pipe 15 on the reactor bottom; a liquid recycle nozzle connected with pipe 5 on the reactor bottom; a gaseous recycle nozzle connected with pipe 3 on the reactor base; a purge nozzle connected with pipe 13 at the reactor top; and an overflow downcomer connecting the top of the reactor R with stripper or heat exchanger $HE_2$;

(b) a first stripper, consisting of a vertical tube bundle heat exchanger $HE_1$ with inlet from the bottom, connected with a gas-liquid separator tank 17, where the separation of a gas phase from the liquid phase occurs;

(c) a second stripper, consisting of a second heat exchanger $HE_2$, equipped with a nozzle for the introduction of the stripping agent, and connected with pipe 2 and arranged in the lower part of the device, this said second stripper being preferably a tube bundle falling film heat exchanger; and (d) a condenser C for the gases flowing from the second stripper.

When the synthesis is performed in two different reaction zones, the reactor R is subdivided, as shown in FIG. 2, into two superimposed sections, an upper reactor section $R_u$ and a lower reactor section $R_L$. It is then provided with suitable means for the alternative or simultaneous introduction into the two sections, through pipes 1 and/or 19, of a feed stream of $NH_3$ coming from the header 20, with another inlet nozzle for $CO_2$ connected to pipe 15 communicating with the bottom of the upper section $R_u$, a liquid recycle nozzle connected to pipe 5 communicating with the bottom of the upper section $R_u$, a gaseous recycle nozzle connected to pipe 3 communicating with the bottom of the upper section $R_u$, a purge nozzle connected to pipe 13 at the top of the upper section $R_u$, an outlet nozzle for the reaction product connected to pipe 4 at the top of the lower section $R_L$, and an overflow-downcomer 18 which directly connects the head of the upper section $R_u$ with the bottom of the lower section $R_L$.

The apparatus just mentioned may include some additional features; for instance, thin-layer heat exchangers both for the condenser C as well as for the first stripper or heat exchanger $HE_1$ and a vertical tube bundle heat exchanger (with inlet from the bottom) for the second stripper $HE_2$. Moreover, if desired, the two sections of the reactor R may consist of two separate reactors provided these are superimposed one over the other, i.e., one disposed at a higher level than the other. However, the use of a single reactor with two overlying sections, according to a preferred arrangement of this invention, allows one to avoid bulky and cumbersome scaffoldings usually required for the superelevation of the reactors with respect to the succeeding equipment which is provided for the subsequent treatment of the effluent coming from the synthesis.

Should it be desired to provide for a supplemental ammonia injection into the first stripper $HE_1$, this stripper is then (as shown in FIGS. 3 and 4) provided with a further nozzle in the lower portion of the first stripper connected to pipe 21 which in turn communicates with the $NH_3$ line 20.

The following examples are given in order still better to illustrate this invention, but without implying any unnecessary limitation thereof.

EXAMPLE 1

The following data refer to a plant having an output capacity of 350 tons per day of urea according to FIG. 1.

The urea is synthesized at a pressure of 200 kg/cm$^2$ and at 190° C. in a vertical cylindrical reactor R equipped with sieve trays adapted to maintain a homogeneous axial flow through the reactor thus avoiding undesirable back-mixing of the reaction liquid. The $NH_3:CO_2$ molar ratio in the reactor is about 5 and the $H_2O:CO_2$ molar ratio is around 0.5. An overall yield of 75% is obtained.

The intermediate liquid product overflows, due to gravity, through pipe 4, into a vertical tube bundle heat exchanger $HE_1$ with inlet from the bottom, heated to 210° C. by steam introduced via line 10, where the residual ammonium carbamate is almost completely decomposed.

The decomposition gases and a portion of the excess $NH_3$ are recycled back to the reactor through gas-liquid separator 17 and pipe 3. The solution 6 flowing out of gas-liquid separator 17, connected to the top of the exchanger $HE_1$, passes to a second exchanger $HE_2$, a falling film stripper, heated with steam introduced via line 11. In this second exchanger $HE_2$, about 75% of the required $CO_2$, preheated to 200° C. in preheater $PH_1$, removes almost all of the residual $NH_3$ and the resulting solution flowing out from the bottom passes through pipe 7 to further and conventional process steps for the urea product.

In the second stripper $HE_2$ the temperature at the top is about 210° C. and the pressure about 200 kg/cm$^2$. The gaseous stream leaving the top of the second stripper $HE_2$ via line 9 flows into a condenser C together with the gases coming from the reactor top via line 13 together with a solution (via line 8) coming from later process steps to which the product urea has been subjected. The condensation heat allows the production of steam in the condenser C which leaves via line 12 for use elsewhere in the plant.

Residual gases containing inert substances (for instance nitrogen) are purged from the condenser C through pipe 14, while the solution to be recycled to the reactor R flows out of the condenser by gravity, the condenser being at 170° C., through pipe 5.

The $NH_3$ feed, preheated in the preheater $PH_2$, is conveyed to the reactor R through pipe 1. Through pipe 15, branching off from $CO_2$ header 16, the remaining 25% of the required $CO_2$ is fed directly to the reactor without preheating.

The reactor is fed with:

7,878 kg of ammonia, preheated to 140° C., through pipe 1, 22,093 kg of ammonium carbamate solution, at 170° C., through pipe 5, and having the following composition:
$NH_3$: 46.31% by weight
$CO_2$: 43.28% by weight
$H_2O$: 10.41% by weight 11,607 kg of vapors at 200° C., through pipe 3, and having the following composition:
$NH_3$: 78.69% by weight
$CO_2$: 16.24% by weight
$H_2O$: 4.64% by weight
inerts: 0.43% by weight 2,570 kg of $CO_2$, at 100° C., through pipe 15.

Through pipe 4, 43,609 kg of urea solution, at 190° C., and having the following composition, leave the reactor R:

$NH_3$: 42.98% by weight
$CO_2$: 8.00% by weight
$H_2O$: 16.29% by weight urea: 32.69% by weight
inerts: 0.04% by weight Through pipe 6, 32,035 kg of urea solution at 210° C., having the following composition, flow out from the first stripper HE₁:
$NH_3$: 30.00% by weight
$CO_2$: 5.00% by weight
$H_2O$: 20.50% by weight
urea: 44.50% by weight Beside the urea solution, 7,888 kg of $CO_2$ (preheated to 200° C. in the preheater $PH_1$) enter the second stripper $HE_2$ through pipe 2, while 23,042 kg of urea solution having the following composition flow out at 210° C. from the second stripper $HE_2$ via line 7:
$NH_3$: 5.97% by weight
$CO_2$: 4.97% by weight
$H_2O$: 27.20% by weight
urea: 61.86% by weight as well as 16,879 kg of vapors at 210° C. having the following composition via line 9:
$NH_3$: 48.79% by weight
$CO_2$: 49.10% by weight
$H_2O$: 1.78% by weight
inerts: 0.33% by weight The heat requirements for the strippers $HE_1$ and $HE_2$ are met by sending thereto through pipe 10, 5,700 kg and, through pipe 11, 2,800 kg of saturated steam at 20 kg/cm² absolute. 11,800 kg of steam at 6 kg/cm² absolute are generated in the ammonium carbamate condenser C.

EXAMPLE 2

Example 1 was repeated utilizing, as the first stripper $HE_1$, a vertical tube-bundle falling film exchanger.

Results analogous with those of Example 1 were obtained.

EXAMPLE 3

The data that follow refer to a plant having an output capacity of 240 tons per day of urea according to FIG. 2.

The urea is synthesized at a pressure of 200 kg/cm² and 190° C. in a vertical cylindrical reactor subdivided into two overlying sections $R_u$ and $R_L$ fitted with sieve trays which maintain steady homogeneous axial flow, avoiding back-mixing of the reaction liquid.

The $NH_3$:$CO_2$ molar ratio in the uppermost section $R_u$ of the reactor is about 5 while the $H_2O$:$CO_2$ molar ratio is maintained around 0.5. The overall yield is 78%.

The intermediate liquid product overflows by gravity into the underlying reactor section $R_L$ through pipe 18, and from this lower section it passes then, through pipe 4, into heat exchanger $HE_1$ through a bottom inlet, this heat exchanger $HE_1$ being heated up to 210° C. by steam introduced via line 10, whereby the residual ammonium carbamate is almost totally decomposed, the decomposition gases and part of the excess $NH_3$ flowing back into the reactor via separator 17 and pipe 3.

Solution flowing out of the bottom of separator 17 via line 6 flows into a second (thin-layer) heat exchanger $HE_2$ heated by steam introduced via line 11. In this second exchanger $HE_2$, 80% of the required $CO_2$, preheated to 200° C. in the preheater $PH_1$ and introduced via lines 16 and 2, removes almost the whole of the residual $NH_3$, while the solution coming from the bottom flows through pipe 7 towards further and usual steps applied to the urea product. In the second heat exchanger $HE_2$ there is a top temperature of about 210° C. and a pressure of about 200 kg/cm².

The gaseous stream which leaves the head of the second heat exchanger $HE_2$ flows into a condenser C via line 9 together with the gases coming from the head of the reactor via line 13 and with a solution of urea coming from the later steps of the process to which the urea product has been subjected. The condensation heat allows the production of steam in the condenser C which leaves via line 12. The purge of the residual gases from the condenser C leaves this latter through pipe 14, while the solution to be recycled to the reactor leaves the condenser by gravity at 170° C. through pipe 5.

The required $NH_3$ is preheated in the preheater $PH_2$ and then fed to the bottom of the upper reactor section $R_u$ through pipe 1 coming from header 20. The remaining 20% of the required $CO_2$ is directly fed, without preheating, to the bottom of the upper reactor section $R_u$ through pipe 15 which branches off the main header 16.

The reactor is fed with:
5,670 kg of pre-heated ammonia, at 140° C., through pipe 1,
15,330 kg of ammonium carbamate solution, at 170° C., through pipe 5,
showing the following composition:
$NH_3$: 44.1% by weight
$CO_2$: 45.3% by weight
$H_2O$: 10.6% by weight
7,110 kg of vapors at 200° C., through pipe 3, showing the following composition:
$NH_3$: 80.5% by weight
$CO_2$: 13.3% by weight
$H_2O$: 6.2% by weight
1,500 kg of $CO_2$, at 100° C., through pipe 15.

From the top of the lower reactor section $R_L$, through pipe 4, there flow out 29,610 kg of urea solution, at 190° C., having the following composition:
$NH_3$: 42.4% by weight
$CO_2$: 6.9% by weight
$H_2O$: 17.1% by weight
urea: 33.8% by weight From the first stripper $HE_1$ there flow out, at 210° C., through pipe 6, 22,500 kg of urea solution having the following composition:
$NH_3$: 30% by weight
$CO_2$: 5% by weight
$H_2O$: 20.5% by weight
urea: 44.5% by weight Into the second stripper $HE_2$ there flow in, besides the urea solution, 5,830 kg of $CO_2$ (preheated to 200° C. in the preheater $PH_1$) through pipe 2, while through pipe 7 there flow out 16,080 kg of urea solution, at 200° C., having the following composition:
$NH_3$: 6.0% by weight
$CO_2$: 5.0% by weight
$H_2O$: 26.8% by weight
urea: 62.2% by weight while 12,250 kg of vapors, at 200° C., flow out through pipe 9, showing the following composition:
$NH_3$: 47.2% by weight
$CO_2$: 50.1% by weight
$H_2O$: 2.7% by weight The heat requirements for the strippers $HE_1$ and $HE_2$ are met by sending 3,400 kg, through pipe 10, and 1,900 kg, through pipe 11, of saturated steam at 20 kg/cm² absolute.

In the ammonium carbamate condenser C 9,000 kg of steam are produced, at 6 kg/cm² absolute.

EXAMPLE 4

Example 3 was repeated using as first stripper $HE_1$ a thin-layer heat exchanger like the one used for the second stripping stage.

In this way the same results were obtained as in Example 3, which were altogether satisfactory.

EXAMPLE 5

Example 3 was repeated, this time feeding the whole of the $NH_3$ (preheated to 170° C. in the preheater $PH_2$) to the base of the lower section $R_L$ of the reactor, through lines 20 and 19.

In this way it was possible to attain an $NH_3:CO_2$ molar ratio in said lower section of 7:1, obtaining an 80% conversion yield of urea.

EXAMPLE 6

Example 5 was repeated using as the first stripper $HE_1$ a vertical tube bundle heat exchanger of the falling film type, having a nozzle (for the introduction of the effluent coming from the reactor) fitted in the head or top of the heat exchanger and a nozzle for the outflow of the product, connected to pipe 6, on the lower portion of the said heat exchanger.

In this way results were obtained analogous to those of Example 5.

EXAMPLE 7

Example 4 was repeated, but this time sending 45% of the pre-heated ammonia feed (at 170° C.) to the base of the lower reactor section $R_L$, while the remaining part was conveyed (at 140° C.) to the base of the uppermost reactor section $R_u$.

In this way results were obtained that were intermediate between the results of Example 4 and the results of Example 6.

EXAMPLE 8

The following data refer to a plant having an output capacity of 350 tons per day of urea according to FIG. 3.

The urea is synthesized at a pressure of 200 kg/cm² and at 190° C. in a vertical cylindrical reactor R provided with sieve trays which maintain the axial flow therethrough homogeneus, thus avoiding back-mixing of the reaction liquid. The $NH_3:CO_2$ molar ratio in the reactor is about 5 and the $H_2O:CO_2$ molar ratio is around 0.5. The intermediate liquid product overflows by gravity through pipe 4 into a vertical falling film heat exchanger, $HE_1$, heated by steam up to 210° C. circulating via lines 10 and 10a, whereby the residual ammonium carbamate is almost completely decomposed with the aid of a stream of ammonia pre-heated at 200° C. in preheater $PH_3$, introduced via line 21, in an amount equal to 50% of the stoichiometric requirement.

The decomposition gases and a portion of the excess $NH_3$ are recycled back to the reactor R through pipe 3. The solution flowing out from the heat exchanger $HE_1$ via line 6 passes to a second heat exchanger $HE_2$, a falling film stripper, heated with steam via lines 11 and 11a. In this second exchanger $HE_2$, 75% of the required $CO_2$, preheated to 200° C. in preheater $PH_1$, removes almost all the residual $NH_3$ and the solution flowing out from the bottom through pipe 7, passes to further and usual process steps for the urea product.

In the second stripper $HE_2$ the temperature at the top is about 210° C. and the pressure about 200 kg/cm².

The gaseous stream leaving the top of the second stripper $HE_2$ via line 9 flows into a condenser C together with the gases coming from the top of the reactor R via line 13 and with a solution of urea coming from successive process steps via line 8.

The condensation heat allows the production of steam in the condenser C, leaving via line 12. Residual gases are purged from the condenser C through pipe 14, while the solution recycled to the reactor R leaves the condenser C by gravity at 170° C. through pipe 5.

The remaining 50% portion of the $NH_3$ feed, preheated at 140° C. in preheater $PH_2$, is conveyed to the reactor R through pipe 1. Through pipe 15, branching off from header 16, the remaining 25% of the required $CO_2$ is directly fed to the reactor R without preheating.

The reactor R is fed with:
3,939 kg of ammonia preheated at 140° C., through pipe 1,
24,778 kg of ammonium carbamate solution at 170° C., through pipe 5,
having the following composition:
   $NH_3$: 51.7% by weight
   $CO_2$: 39.0% by weight
   $H_2O$: 9.3% by weight
13,008 kg of vapors at 210° C., through pipe 3,
having the following composition:
   $NH_3$: 81.3% by weight
   $CO_2$: 14.5% by weight
   $H_2O$: 4.2% by weight
2,537 kg of $CO_2$ at 100° C., through pipe 15.

Through pipe 4, 43,593 kg of urea solution, at 190° C., having the following composition, leave the reactor R:
   $NH_3$: 43.0% by weight
   $CO_2$: 8.0% by weight
   $H_2O$: 16.3% by weight
   urea: 32.7% by weight Through pipe 21, a stream of 3,939 kg of ammonia pre-heated at 200° C. enters the first stripper $HE_1$, wherefrom, through pipe 6, 34,523 kg of urea solution having the following composition flow out:
   $NH_3$: 35.0% by weight
   $CO_2$: 4.6% by weight
   $H_2O$: 19.0% by weight
   urea: 41.4% by weight Besides the urea solution, 7,847 kg of $CO_2$ enter the second stripper $HE_2$ through pipe 2, while through pipe 7, 23,043 kg of urea solution having the following composition flow out at 210° C.:
   $NH_3$: 6.0% by weight
   $CO_2$: 5.0% by weight
   $H_2O$: 27.1% by weight
   urea: 61.9% by weight
as well as, through pipe 9, 19,328 kg of vapors at 210° C. having the following composition:
   $NH_3$: 55.7% by weight
   $CO_2$: 42.7% by weight
   $H_2O$: 1.6% by weight The heat requirements for the strippers $HE_1$ and $HE_2$ are met by sending thereto, through pipe 10, 6,300 kg and, through pipe 11, 2,600 kg of saturated steam at 20 kg/cm² absolute. 12,000 kg of steam at 6 kg/cm² absolute are generated in the ammonium carbamate condenser C.

The overall conversion yield is comparable to that of Example 1.

EXAMPLE 9

Example 8 was repeated by feeding 100% of the required $CO_2$ to the second stripper $HE_2$.

Results analogous to those of Example 8 were obtained.

EXAMPLE 10

The following data refer to a plant having an output of 240 tons per day of urea according to FIG. 4.

The urea is synthesized at 200 kg/cm$^2$, and at 190° C., in a vertical cylindrical reactor subdivided into two overlying sections $R_u$ and $R_L$ fitted with sieve trays which maintain homogeneous axial flow therethrough, thus avoiding back-mixing of the reaction liquid.

The $NH_3:CO_2$ molar ratio in the upper section $R_u$ of the reactor is about 5, while the $H_2O:CO_2$ molar ratio is around 0.5.

The intermediate liquid product flows over by gravity into the underlying section $R_L$ through pipe 18 and from there it passes, through pipe 4, and after a residence time of about 6 minutes in $R_L$, into a first vertical thin-layer tube bundle heat exchanger $HE_1$ of the falling film type, heated with steam up to 210° C. via lines 10 and 10a, in which the residual ammonium carbamate is almost totally decomposed, also by the help of an ammonia stream, pre-heated at 180° C. in the preheater $PH_3$, equal to about 50% of the stoichiometric requirement. The decomposition gases and part of the $NH_3$ excess flow back to the bottom of the upper reactor section $R_u$ through pipe 3.

The solution which flows out through the bottom of the first heat exchanger $HE_1$ passes via line 6 into a second heat exchanger $HE_2$, likewise of the thin-layer type, heated with steam via lines 11 and 11a.

In this second heat exchanger $HE_2$ about 80% of the $CO_2$ requirement, pre-heated at 200° C. in preheater $PH_1$ and introduced via line 2, removes almost the whole of the residual $NH_3$ and the solution flowing out of the bottom passes through pipe 7 to further and usual steps for the processing the urea product.

In the second heat exchanger $HE_2$ there are a top temperature of about 210° C. and a pressure of about 200 kg/cm$^2$.

The gaseous stream which leaves the top of the second heat exchanger $HE_2$ via line 9 passes to a condenser C together with purge gases coming from the head of the upper reactor section $R_u$ via line 13 and with a solution of urea coming from further steps of the process via line 8. The condensation heat allows the production of steam in the condenser C, leaving via line 12. The residual gases are purged through pipe 14 while the solution to be recycled back to the upper reactor section $R_u$, leaves the condenser C by gravity, at 170° C., through pipe 5.

The remaining part of the $NH_3$ feed preheated at 140° C. in preheater $PH_2$, is sent to the upper reactor section $R_u$ through pipe 1. By means of pipe 15, branching from header 16, the residual 20% of the required $CO_2$ is fed directly into the upper reactor section $R_u$ without any pre-heating.

The reactor is fed with:
3,000 kg of pre-heated ammonia at 140° C., through pipe 1,
16,210 kg of ammonium carbamate solution at 170° C., through pipe 5,
having the following composition:
$NH_3$: 47.8% by weight
$CO_2$: 42.1% by weight
$H_2O$: 10.1% by weight
8,900 kg of vapors at 200° C., through pipe 3, of the following composition:
$NH_3$: 83.2% by weight
$CO_2$: 11.9% by weight
$H_2O$: 4.9% by weight
1,500 kg of $CO_2$ at 100° C., through pipe 15.

From the upper part of the lower reactor section $R_L$, through pipe 4, there flows out 29,610 kg of urea solution at 190° C., showing the following composition:
$NH_3$: 42.4% by weight
$CO_2$: 6.9% by weight
$H_2O$: 17.1% by weight
urea: 33.8% by weight A stream of 2,670 kg of ammonia, pre-heated at 180° C., enters through pipe 21 the bottom of the first stripper $HE_1$ from which flow out through pipe 6, 23,380 kg of urea solution showing the following composition:
$NH_3$: 32.1% by weight
$CO_2$: 4.3% by weight
$H_2O$: 20.8% by weight
urea: 42.8% by weight Besides the urea solution from the first stripper $HE_1$, into the second stripper $HE_2$ enter 5,830 kg of $CO_2$ flowing in through pipe 2, while from the same stripper $HE_2$ flow out at 200° C., through pipe 7, 16,080 kg of urea solution showing the following composition:
$NH_3$: 6.0% by weight
$CO_2$: 5.0% by weight
$H_2O$: 26.8% by weight
urea: 62.2% by weight
and 13,130 kg of vapors at 200° C., through pipe 9, showing the following composition:
$NH_3$: 51.7% by weight
$CO_2$: 45.6% by weight
$H_2O$: 2.3% by weight The heat requirements for the strippers $HE_1$ and $HE_2$ are met by sending 3,600 kg through pipe 10 and 2,000 kg through pipe 11 respectively, of saturated steam at 20 kg/cm$^2$ absolute. In the ammonium carbamate condenser C are produced 9,200 kg of steam at 6 kg/cm$^2$ absolute.

The whole conversion yield in the reactor in this embodiment is about 78%.

EXAMPLE 11

Example 10 was repeated, but this time feeding 100% of the $CO_2$ into the second stripper $HE_2$.

Nearly the same results were obtained as in Example 10.

EXAMPLE 12

Example 10 was repeated, but this time feeding 50% of the $NH_3$ feed preheated at 170° C. to the base of the lower section $R_L$ of the reactor through pipe 19.

In this way it was possible to attain an $NH_3:CO_2$ molar ratio in said lower section $R_L$ equal to 7:1, thus obtaining a yield of about 80%.

EXAMPLE 13

Example 10 was repeated, but this time sending 25% of the ammonia feed preheated at 170° C. to the base of the lower section $R_L$ of the reactor and the same quantity of ammonia preheated at 140° C. to the base of the upper section $R_u$.

In this way intermediate results lying between the results of Example 10 and the results of Example 12 were obtained.

What is claimed is:

1. An improved isobaric double-recycle process for synthesizing urea with the formation of ammonium carbamate as an intermediate, comprising effecting reaction between ammonia and carbon dioxide at high $NH_3:CO_2$ molar ratios, a heat-treatment of the synthesis product at substantially the same pressure as that of the synthesis step and in the presence of a stripping gas, and two distinct isobaric recycles of the residual substances and of the substances in excess released from said synthesis product, said process being characterized in that:

(a) said heat-treatment of the synthesis product is carried out in two consecutive stages which are isobaric or substantially isobaric with respect to the synthesis step, in the first of which stages said synthesis product is heated, whereby substantially all the residual ammonium carbamate is decomposed and the decomposition products are displaced together with part of the excess $NH_3$, while in the second stage the remaining part of the $NH_3$ excess is displaced by supplying supplemental heat and by injecting thereto a $CO_2$ stream; and (b) the gas phase stripped in the first stage is immediately recycled to the synthesis step and the gas phase stripped in the second stage is subjected to a condensation and to a residual gas purge and then recycled, in the liquid state, to the synthesis step.

2. A process according to claim 1, wherein the synthesis temperature ranges from 170° to 205° C.

3. A process according to claim 1, wherein the synthesis temperature ranges from 180° to 200° C.

4. A process according to claim 1, wherein the synthesis pressure is between 100 and 250 $Kg/cm^2$.

5. A process according to claim 1, wherein the synthesis pressure is between 180 and 225 $Kg/cm^2$.

6. A process according to claim 1, wherein the ammonia feed is preheated and the $CO_2$ stream, fed to the second treatment stage, is between 10 and 100% of the total synthesis requirement.

7. A process according to claim 6, wherein the $CO_2$ stream fed to the second treatment stage (second stripping) is from 50 to 90% of the total synthesis requirement, the remaining part being fed directly to the synthesis step or to the first treatment stage (first stripping).

8. A process according to claim 1, wherein the synthesis of urea is carried out in two different, subsequent and superimposed zones, to the first of which, overlying the second, the two isobaric recycles are fed, whereby the dehydration to urea of the most part of the ammonium carbamate is there performed, while in the second zone, operating according to $NH_3:CO_2$ molar ratios equal to or higher than those of the preceding zone, the completion of the dehydration to urea is carried out, substantially until reaching the equilibrium level.

9. A process according to claim 8, wherein the synthesis is performed in two different superimposed zones and wherein said $NH_3:CO_2$ ratio is from 4:1 to 7:1 in the first and uppermost zone and from 5:1 to 8:1 in the second zone.

10. A process according to claim 9, wherein the excess of ammonia solubilized in the liquid phase is recovered in the first of the two stripping stages and then fed to the uppermost synthesis zone, an intermediate value of the $NH_3:CO_2$ molar ratio between 5:1 and 8:1 being obtained by feeding a part of the pre-heated ammonia to the uppermost zone and a part of the lowermost zone.

11. A process according to claim 10, wherein the temperature of the $NH_3$ feed to the lowermost zone is higher with respect to that fed to the uppermost zone.

12. A process according to claim 1, wherein during the stripping of the excess $NH_3$ in the first stage of the isobaric treatment a predetermined amount of ammonia is injected into the solution to be stripped.

13. A process according to claim 1, wherein the $NH_3:CO_2$ molar ratio during the synthesis ranges from 2.5:1 to 10:1.

14. A process according to claim 13, wherein the synthesis is performed in two different superimposed zones and wherein said $NH_3:CO_2$ ratio is from 4:1 to 7:1 in the first and uppermost zone and from 5:1 to 8:1 in the second zone.

15. A process according to claim 1, wherein the $NH_3:CO_2$ molar ratio during the synthesis ranges from 4:1 to 7:1.

* * * * *